United States Patent [19]

Chakrabarti et al.

[11] 4,405,799

[45] Sep. 20, 1983

[54] TREATMENT OF EFFLUENTS CONTAINING DIOXANE

[75] Inventors: Paritosh M. Chakrabarti, Cedar Grove; Mohamed M. Hashem; Tom M. H. Cheng, both of Wayne, all of N.J.

[73] Assignee: GAF Corporation, New York, N.Y.

[21] Appl. No.: 291,740

[22] Filed: Aug. 10, 1981

[51] Int. Cl.³ .................. C07D 319/06; C07D 319/12
[52] U.S. Cl. ..................................... 549/369; 549/377
[58] Field of Search .............................. 549/377, 369

[56] References Cited

U.S. PATENT DOCUMENTS 4,283,339  8/1981  Godfrey .............................. 549/377
4,285,881  8/1981  Yang .................................... 549/377

FOREIGN PATENT DOCUMENTS 49-39268  10/1974  Japan .................................. 549/377

Primary Examiner—Ethel G. Love
Attorney, Agent, or Firm—Marilyn J. Maue; J. Gary Mohr; Joshua J. Ward

[57] ABSTRACT

The invention relates to the treatment to remove dioxane from gaseous effluents by contacting the effluent with a concentrated acid having a $pK_1$ value of not more than 5 to complex the dioxane with acid preliminary to venting the treated gaseous effluent to the atmosphere and disposing of the complex wherein the dioxane is concentrated.

15 Claims, No Drawings

TREATMENT OF EFFLUENTS CONTAINING DIOXANE

BACKGROUND OF THE INVENTION

Although dioxanes have been widely used as solvents for various chemicals and are generally present as impurities in certain surfactants, such as alcohol and alkyl phenol ethoxylates and derivatives thereof, such as sulfate, sulfonate and phosphate esters, recent evidence of animal carcinogenic and other harmful properties has discouraged their unencumbered utilization. Accordingly, when plants, or animals are exposed to products containing polyoxyethylene compounds, the dioxane impurity must be significantly reduced to very low levels, preferably less than about 5 ppm. When a small amount of the dioxane impurity is present in pharmaceutical or cosmetic formulations, even more stringent purification is desired for its removal below the current detection limit of about 0.5 ppm.

Small quantities of dioxane are also formed in the reaction of ethylene oxide with an acitve hydrogen atom containing compound such as an alkylphenol, mercaptan, amine, acid, etc. to produce ethoxylated products which find widespread application as emulsifiers, dispersants and foaming agents. Objectionable amounts of dioxane from these sources are often present in these final products, thus presenting a potential health hazard.

Several processes for the removal of this troublesome contaminant from products of manufacture have been proposed, namely sparging alkoxylated products, e.g. ethoxylated compounds, with nitrogen, air or steam; however, such methods have not resulted in adequate removal of the contaminant from waste gases to insure safe exposure and venting of the waste gas, containing the dioxane to the atmosphere, remains a serious problem.

Accordingly, the present process is directed to removal of dioxane from effluent waste gases for safe release of the treated gas to the atmosphere and to containment of the dioxane in a concentrated state for reduced volume storage or safer disposal by incineration, chemical conversion or by other suitable means.

Hence, it is an object of the present invention to remove dioxane from various waste gases to a level such that the gases may be safely vented to the atmosphere and to provide an economical and efficient process for accomplishment of this purpose.

Another object is to provide a process for recovering dioxane from waste gases in a substantially non-volatile and concentrated, chemically complexed form.

Still another object of this invention is to provide a process for removing dioxane from waste gases to less than 0.5 ppm before venting to the atmosphere.

These and other objects will become apparent from the following description and disclosure.

DESCRIPTION OF THE INVENTION

According to the invention, a waste gas containing dioxane in amounts in low concentration, as low as 0.001 ppm and in concentrations up to about 25%, is contacted with a strong, concentrated acid having an acid strength $pK_1$ value of not more than about 5. More particularly, the dioxane to be removed from the gas is beneficially contacted with a high molar excess of acid, in excess of 1:1 and up to 2,000 molar excess of acid at a temperature of up to about 150° C., under a pressure of from about 0.1 mm Hg and about 10,000 mm Hg. Preferably, from an economic and engineering standpoint, the dioxane in the waste gas is contacted with between about 5 and about 1,000 molar excess of acid at a temperature of between about 0° C. and about 110° C. under from about 760 mm to about 2,000 mm Hg, and the acid has a $pK_1$ value of between about $-3$ and about 3.

The acid may be used in a pure or diluted state and combinations of acids may be usefully employed either in the liquid phase or as acid deposited on an inert solid carrier. Thus, contacting can be effected in a tank containing acid in the liquid state or in an adsorption zone such as a packed or trayed tower containing acid impregnated or deposited on a particulate inert carrier. Suitable acid supports include activated carbon, e.g. activated charcoal, alkaline earth silicates, silica, or other conventional inert porous material in the form of pellets, beads, flakes, granules and the like.

In certain cases, where the acid is highly viscous, dilution with an appropriate solvent or a liquid co-acid is recommended. Suitable solvents for acid dilution include water, alcohols, liquid alkanes, benzene, toluene and other solvents having a boiling point above the temperature of contacting. Generally dilution of the acid should not exceed 50% since most beneficial results are obtained with the acid in a concentrated state.

As stated above combinations of acids may be used in admixture. For example such mixtures include sulfuric/phosphoric acids; trichloroacetic/acetic acids; methanesulfonic/sulfuric acids; and phosphoric/polyphosphonic/hypophosphoric acids. Solid acid agents, such as trichloroacetic acid and others having a $pK_1$ value of not more than 5 are also suitably employed with a diluent or a liquid co-acid to provide a liquid phase.

Some examples of suitable acids which may be employed to complex with dioxane from the waste gases of the present process include the following.

| | Formula | $pK_1$ value | Preferred range of % Acid Conc. |
|---|---|---|---|
| Organic Acids | | | |
| succinic | $HOOC(CH_2)_2COOH$ | 4.16 | 85–100 |
| acetic | $CH_3-COOH$ | 4.75 | 85–100 |
| chloroacetic | $ClCH_2-COOH$ | 2.85 | 85–100 |
| dichloroacetic | $Cl_2CH-COOH$ | 1.48 | 75–100 |
| trichloroacetic | $Cl_3C-COOH$ | 0.70 | 75–100 |
| methanesulfonic | $CH_3SO_3OH$ | 2.85 | 85–100 |
| 2,4,6-trinitrophenol | $(NO_2)_3C_6H_2OH$ | 0.38 | 70–100 |
| benzosulfonic | $C_6H_5-SO_2OH$ | 0.70 | 80–100 |
| napthalenesulfonic | $C_{10}H_7-SO_2OH$ | 0.57 | 80–100 |
| oxalic | $HOOC-COOH$ | 1.23 | 85–100 |
| Inorganic Acids | | | |
| iodic | $HIO_3$ | 0.77 | 80–100 |
| periodic | $HIO_4-2H_2O$ | 1.55 | 80–100 |
| perchloric | $HClO_4$ | $-7.3$ | 70–100 |
| chlorous | $HClO_2$ | 1.96 | 80–100 |
| hydroiodic | $HI$ | $-9.5$ | 65–100 |
| hydrochloric | $HCl$ | $-6.1$ | 65–100 |
| hydrofluoric | $HF$ | 3.45 | 90–100 |
| hydrobromic | $HBr$ | $-9.0$ | 65–100 |
| selenic | $H_2SeO_4$ | $-3$ | 70–100 |
| polyphosphoric | $HO-\overset{O}{\underset{OH}{P}}-(O-\overset{O}{\underset{OH}{P}})_{\overline{n}}OH$ | 2.12 | 85–115 |

| | Formula | pK$_1$ value | Preferred range of % Acid Conc. |
|---|---|---|---|
| hypophosphorous | HPH$_2$O$_2$ | 1.1 | 80–100 |
| pyrophosphoric | H$_4$P$_2$O$_7$ | 0.85 | 80–100 |
| phosphoric | H$_3$PO$_4$ | 2.12 | 75–100 |
| phosphorous | H$_3$PO$_3$ | 2.0 | 85–100 |
| sulfuric | H$_2$SO$_4$ | −3.0 | 75–100 |
| sulfurous | H$_2$SO$_3$ | 1.81 | 85–100 |
| chlorosulfonic | HOSO$_2$Cl | −10.43 | 55–100 |
| thiosulfuric | H$_2$S$_2$O$_3$ | 0.60 | 70–100 |

Of the above acids, sulfuric acid is most preferred for its ability to complex with dioxane. In regard to organic acids, those having pK$_1$ values higher than +2.85 are used for waste gases of lower dioxane content, desirably containing less than 1 weight % dioxane.

The waste gases referred to for processing in this invention may contain as little as 0.001 ppm or lower and as high as 20,000 ppm or higher dioxane and are obtained from sources which form dioxane or substituted dioxanes as by-products of reactions or from reactions which employ dioxane as a solvent, reaction promotor, or carrier and where amounts of the contaminant are carried over into the final product. In such processes, the product is generally subjected to vacuum distillation or sparging with a suitable gas such as nitrogen, air, carbon dioxide or steam to release a major portion of the dioxane in the waste gas which is separated from the liquid product. Specific examples of processes producing such waste gases include the extraction of dioxane from an alkoxylated product, e.g. the polyoxyalkylene products including polyoxyethylene- and polyoxypropylene-glycols, and derivatives thereof, such as phosphate esters and sulfate esters. The present process is also capable of removing substituted dioxanes, such as methyl and dimethyl dioxanes from waste gases containing them. Such waste gases vented from product recovery may be passed directly into the present acid contacting zone wherein the acid forms an innocuous complex with dioxane. The treated waste gas effluent can then be safely vented to the atmosphere. The present process is particularly adapted to the treatment of waste gases from the process for preparing dioxane-free polyoxyethylene phosphate esters described in co-pending patent application Ser. No. 274,703, entitled THE METHOD OF REMOVING DIOXANE FROM PHOSPHATE ESTER SURFACTANTS, now U.S. Pat. No. 4,375,437 wherein any residual phosphoric acid in the phosphate ester product is neutralized with a base, preferably sodium hydroxide, so as to liberate the dioxane in the gaseous phase and prevent recombination with the phosphoric moiety.

The waste gases treated by the present process often contain substantial quantities of water which dilute and weaken the acid solution; accordingly, the acid must be replaced or reconstituted when the dioxane concentration in the exit gas increases to an undesirable level. Sulfuric acid has been found to be effective over a relatively broad concentration range including acid concentration as low as 65%, although it is preferred to maintain a concentration above about 70%.

The present process is carried out in an acid resistant tank or packed tower containing the acid solution or acid impregnated solid particles. The waste gas is bubbled through the acid solution or passed through the packed column over a period sufficient to remove dioxane to the desired level whereupon the exit gases are vented to the atmosphere. During contact, the dioxane is complexed with the acid in a non-volatile form which is readily disposable or which can be recovered for further use.

In commercial practice, towers packed with acid treated absorbents can be continuously operated by passing the dioxane containing gas through the towers employed alternately or in series. Alternatively, dioxane containing gas can be bubbled through a tank containing acid solution. Generally, to eliminate rapid depletion and replacement, sizable tanks containing large acid inventories are preferred for waste gases containing higher level concentrations of dioxane or large volumes of such waste gas presented for treatment. The dioxane level in the exit gas from the acid treating zone should not exceed 50%, and preferably should not exceed 30%, before replacement or reconcentration of the acid is recommended.

Both methods eventually require acid replacement, reconcentration or contact particle regeneration where the dioxane level in the exit gas exceeds the desired amount.

By the above process employing concentrated acid as a complexing agent for dioxanes, the dioxane can be recovered in a concentrated, state in condition for safe disposal.

Having generally described the process of the present invention, reference is now had to the following Examples which illustrate specific and preferred embodiments of the invention but which are not to be construed as limiting to the scope thereof. All amounts and proportions in the Examples are by weight unless otherwise specified.

EXAMPLE I

The absorbability of sulfuric acid for dioxane at various concentrations was measured as the vapor pressure of dioxane in the acid solutions reported in following Table I. The table shows the equilibrium vapor concentration of dioxane detected above the liquid (head space) using solutions of 1% to 20% dioxane in sulfuric acid of from 100% to 20% acid concentration. In all cases, except where indicated, the temperature of the contacting zone was maintained at about 20° C. and 750 mm Hg pressure was employed.

The samples for head space analysis were prepared by adding dioxane to a 30 ml serum bottle containing acid. All bottles were at a temperature of 20° C. except where indicated. A 10 ml volume of liquid sample was used for all samples. After equilibrating for 2 hours, 500 microliters of vapor in the head space were withdrawn by means of a 1 ml gas tight syringe and the gaseous sample injected into a gas chromatograph equipped with a 4 foot chromosorb 102 column wherein the gas was analyzed for concentration of dioxane in parts per million (ppm).

TABLE I

| Liquid Solution | Dioxane in the Vapor Head Space (ppm) |
|---|---|
| 1% dioxane in water | 470 |
| 5% dioxane in water | 2490 |
| 1% dioxane in sulfuric acid (100%) | none |
| 1% dioxane in 75/25 sulfuric acid/H$_2$O | none |
| 1% dioxane in 50/50 sulfuric acid/H$_2$O | 32 |
| 1% dioxane in 20/80 sulfuric acid/H$_2$O | 470 |
| 10% dioxane in sulfuric acid (100%) | none |

TABLE I-continued

| Liquid Solution | Dioxane in the Vapor Head Space (ppm) |
|---|---|
| 20% dioxane in sulfuric acid (100%) | none |
| 10% dioxane in sulfuric acid, 50° C. | none |
| 10% dioxane in sulfuric acid, 100° C. | none |

EXAMPLE 2

The above procedure was repeated for determining the absorbability of various other acids for dioxane and the results reported in Table II. The contact temperature was maintained at 20° C. and the pressure was 750 mm Hg.

TABLE II

| Liquid Solution | Dioxane in the Vapor Head Space (ppm) |
|---|---|
| 1% dioxane in 85% phosphoric acid | 7 |
| 10% dioxane in 85% phosphoric acid | 42 |
| 1% dioxane in 98% methane sulfonic acid | none |
| 1% dioxane in polyphosphoric acid (100%) | none |
| 1% dioxane in glacial acetic acid | 98 |

From these tables it can be seen that water is a poor absorbent and excessive dilution of acid is not desirable; whereas concentrated liquid acids are excellent absorbents for dioxane. For example, concentrated sulfuric acid shows no detectable dioxane in the vapor phase even at 20% concentration. Acetic acid, having a $pK_1$ value of 4.75 was the least efficient although a considerable amount (about 80%) of the dioxane was retained in the trap.

EXAMPLE 3

This example illustrates the rapidity of dioxane absorption by the present liquid acids. Accordingly, the present process represents a viable approach for dioxane removal under the dynamic conditions in sparging operations.

In a 1-liter 4-necked round bottomed glass flask was charged 600 g of a 100% active liquid alkyl aryl polyoxyethylene phosphate ester (Gafac ® RE-610). The flask was equipped with a stirrer, a nitrogen inlet, a thermometer and an outlet leading to a series of three traps, each containing 120 g of concentrated $H_2SO_4$ (96.5%). Nitrogen gas was bubbled into the flask below the phosphate ester liquid level while heating the flask to maintain a temperature of 95° C., for 1 hour in the first experiment and for 3 hours in the second experiment. The pressure in the flask was 760 mm Hg. The purged gas from the Gafac ® liquid was then passed in series through the traps containing the acid at a temperature of 25° C.

The gas chromatographic analysis of dioxane in the original liquid, in the purged liquid and in the liquid acid in the traps is reported in Table III.

TABLE III

| | Dioxane grams |
|---|---|
| Gafac ® RE-610, original | 0.44 |
| Gafac RE-610, residual in purged liquid, 1 hr., 95° C. | 0.30 |
| Liquid Acid Solution in trap #1, 1 hr. | 0.13 |
| Liquid Acid Solution in trap #2, 1 hr. | none |
| Liquid Acid Solution in trap #3, 1 hr. | none |
| Gafac RE-610, original | 0.44 |
| Gafac RE-610, residual in purged liquid, 3 hr., 95° C. | 0.18 |
| Liquid Acid Solution in trap #1, 3 hr. | 0.24 |
| Liquid Acid Solution in trap #2, 3 hr. | none |
| Liquid Acid Solution in trap #3, 3 hr. | none |

The above example indicates that dioxane impurity is completely retained by the acid in the first trap so that successive traps are unnecessary.

EXAMPLE 4

Example 3 was repeated except the original Gafac ® RE-610 was enriched with 1% dioxane. Total content of dioxane in the sample of Gafac ® was 6.42 grams. The purpose of this example was to determine whether higher concentrations of dioxane could be quickly absorbed in sulfuric acid. Table IV gives the gas chromatographic results of this experiment.

Samples analyzed below were purged with nitrogen at 95° C. for three hours. A second set of samples was purged with nitrogen at 95° C. for six hours. The dioxane removed by purging was treated in three sulfuric acid traps operated in series.

TABLE IV

| 3 Hours Sparging with $N_2$ | Total Dioxane in the Liquid Phase, grams |
|---|---|
| Purged sample | 2.06 |
| Trap #1 | 4.36 |
| Trap #2 | none |
| Trap #3 | none |

| 6 Hours Sparging with $N_2$ | Total Dioxane in the Liquid Phase, grams |
|---|---|
| Purged sample | 1.14 |
| Trap #1 | 5.28 |
| Trap #2 | none |
| Trap #3 | none |

Again, it can be seen from the data of Tables III, IV that substantially all dioxane was retained in trap #1. This indicates, under the dynamic conditions of bubbling $N_2$, that dioxane was instantaneously complexed by the acid in the first trap.

EXAMPLE 5

This example illustrates that the liquid acid deposited on a porous carrier can be used to complex with dioxane.

In a one-liter 4-necked round bottomed glass flask was charged 600 g of Gafac ® RE-610 and the purging process of Example 4, after enrichment with 1% dioxane, was repeated. The resulting liquid was sparged with nitrogen gas at 95° C. for 3 hours under 750 mm Hg before transfer of the sparged gas in series through traps 1 and 2. Trap #1 contained 65 g of an absorbent, manufactured by coating 1 part of 85% $H_3PO_4$ on 2 parts (W/W) of Nuchar WV-B, activated charcoal. Trap #2 contained 90% sulfuric acid to detect any dioxane escaping Trap #1. The gas chromatographic results are reported in Table V.

TABLE V

| Liquid Solution | Total Dioxane grams |
|---|---|
| Gafac ® RE-610, original + 1% dioxane | 6.42 |
| Gafac ® RE-610, + 1% dioxane purged 3 hours at 95° C. | 2.70 |
| First Acid Trap (charcoal) | 3.65* |

TABLE V-continued

| Liquid Solution | Total Dioxane grams |
| --- | --- |
| Second Acid Trap (sulfuric acid) | none |

*amount retained on charcoal

Again all dioxane from the sparged gas is completely and instantaneously retained in the first trap.

EXAMPLE 6

The present acids are capable of removing trace amounts of dioxane from waste gases. Sparging with nitrogen, carbon dioxide or steam cannot be used to efficiently remove such small amounts of the impurity; however, the dioxane level in the air accumulates on continuous venting of such contaminated waste gases and increases the total dioxane content presenting a potential health hazard.

The general procedure described in Example 3 was repeated, except that Igepal® CO 630*, containing 5 ppm dioxane replaced Gafac RE-610, the nitrogen gas was bubbled through the liquid at a flow rate of 100 ml/minute and the temperature in the flask was maintained at 110° C. for 6 hours. As in Example 3, the first acid trap contained 120 g of sulfuric; however, the second and third trap contained only 30 g of the acid. The test results are reported in following Table VI.

*a phenol polyoxyethylene surfactant containing an average of 9 oxyethylene units

TABLE VI

| | Grams of Dioxane |
| --- | --- |
| Igepal CO-630 original | 0.003 |
| Igepal CO-630 after purging with $N_2$ | none |
| Sulfuric acid in Trap #1 | 0.003 |
| Sulfuric acid in Trap #2 | none |
| Sulfuric acid in Trap #3 | none |

It is to be understood that many operational and equipment variations in the above described process will become apparent to those skilled in the art from the above disclosure. Also, any of the conventional purging gases, e.g. air, carbon dioxide, etc. can be substituted for nitrogen in the above examples to provide equivalent results. Additionally, the acid support in Example 5 can be substituted with a wide variety of inert porous supports, particularly porous silica, activated charcoal, alkaline earth silicates etc. to provide the same efficient and complete removal of dioxanes from a gas by complexing with the acid. Finally, in the above examples, other acids, e.g. perchloric, hydrochloric, chlorosulfonic acids, and the aforementioned mixtures of acids, can be substituted to provide substantially complete removal of dioxane from the gaseous effluent.

What is claimed is:

1. A process for removing dioxane from an alkoxylated product waste gas having a dioxane concentration of up to about 25%, which comprises contacting said gas with an acid having a $pK_1$ value of not more than 5 at an acid concentration above 50%.

2. The process of claim 1 wherein the gas is contacted with acid in the liquid state.

3. The process of claim 1 wherein the gas is contacted with the acid at a temperature up to about 150° C. under a pressure of from about 0.1 mm Hg to about 10,000 mm Hg.

4. The process of claim 3 wherein the concentration of dioxane in the waste gas to be treated is between about 0.001 and about 20,000 ppm.

5. The process of claim 3 wherein said acid is sulfuric acid at an acid concentration of from about 65 to about 100 weight %.

6. The process of claim 3 wherein said acid is phosphoric acid at an acid concentration of from about 75 to about 100 weight %.

7. The process of claim 3 wherein said acid is a liquid polyphosphoric acid.

8. The process of claim 3 wherein said acid is methanesulfonic acid at an acid concentration of from about 85 to about 100 weight %.

9. The process of claim 1 wherein the gas is contacted with the acid deposited on a porous support.

10. The process of claim 9 wherein said support is in particulate form.

11. The process of claim 10 wherein said support is activated carbon.

12. The process of claim 10 wherein said support is activated charcoal.

13. The process of claim 10 wherein said support is a porous silica.

14. The process of claim 10 wherein orthophosphoric acid is deposited on said support.

15. The process of claim 10 wherein sulfuric acid is deposited on said support.

* * * * *